United States Patent [19]

Takago et al.

[11] Patent Number: 5,200,440
[45] Date of Patent: Apr. 6, 1993

[54] ORGANOSILICONE-TREATED SILICA AND A COMPOSITION CONTAINING IT

[75] Inventors: Toshio Takago, Annaka; Hiroshi Inomata, Takasaki; Shinichi Sato; Hitoshi Kinami, both of Annaka, all of Japan

[73] Assignee: Shin-Etsu Chemical Co., Ltd., Tokyo, Japan

[21] Appl. No.: 606,870

[22] Filed: Oct. 31, 1990

[30] Foreign Application Priority Data

Nov. 2, 1989 [JP] Japan .................. 1-286388

[51] Int. Cl.$^5$ .............................................. C08K 9/06
[52] U.S. Cl. ...................... 523/213; 523/212; 556/482; 106/490; 524/493; 524/588; 524/863
[58] Field of Search ............... 106/490; 524/863, 588, 524/493; 523/203, 212, 213; 427/219; 556/482

[56] References Cited

U.S. PATENT DOCUMENTS

| | | | |
|---|---|---|---|
| 4,287,114 | 9/1981 | Itoh et al. | 524/493 |
| 4,478,990 | 10/1984 | Kohno et al. | 556/482 |
| 4,728,687 | 3/1988 | Watanabe et al. | 524/493 |
| 4,849,022 | 7/1989 | Kobayashi et al. | 106/490 |
| 4,918,126 | 4/1990 | Matsushita et al. | 524/493 |
| 4,923,520 | 5/1990 | Anzai et al. | 106/490 |
| 4,968,848 | 11/1990 | Kruse et al. | 556/482 |
| 4,983,679 | 1/1991 | Cohen et al. | 525/377 |
| 4,985,477 | 1/1991 | Collins et al. | 106/490 |
| 5,008,305 | 4/1991 | Kennan et al. | 106/490 |

FOREIGN PATENT DOCUMENTS 2-059417 2/1990 Japan .

OTHER PUBLICATIONS

"The Condensed Chemical Dictionary", 7th edition, Reinhold Publishing Corporation, p. 844.

Primary Examiner—John C. Bleutge
Assistant Examiner—Karen A. Dean
Attorney, Agent, or Firm—Oblon, Spivak, McClelland, Maier & Neustadt

[57] ABSTRACT

An organosilicone-treated silica obtained by treating
(A) a silica powder having a specific surface area of at least 50 m$^2$/g with
(B) a triorgano(1-alkoxyvinyloxy)silane having the formula (I):

$$CH_2=\underset{\underset{OR^1}{|}}{C}-O-Si(R^2)_3 \quad (I)$$

wherein R$^1$ is a monovalent hydrocarbon group or an ether linkage-containing organic group, and R$^2$ are each a substituted or unsubstituted monovalent hydrocarbon group or an ether linkage-containing organic group. The invention also discloses an organopolysiloxane composition containing the organosilicone-treated silica and a process preparing the composition. The organosilicone-treated silica is of high quality, containing no substance with disagreeable smell or corrosiveness which has been by-produced heretofore. Hence, the composition containing the silica is free from pseudocrosslinking such as structuring or crepe hardening.

11 Claims, 1 Drawing Sheet

5,200,440

ORGANOSILICONE-TREATED SILICA AND A COMPOSITION CONTAINING IT

BACKGROUND OF THE INVENTION

1. Field of the Invention

This invention relates to an organosilicone-treated silica, a composition containing it, and a process for preparing the composition.

2. Description of the Prior art

For the purposes of regulating fluidability, and reinforcing mechanical strength or improving release property, adhesive property, compression set, heat resistance or chemical resistance, a silica powder is added to an organosilicone composition such as silicone rubbers, silicone greases and silicone oil compounds. Such silica powders include fumed silicas produced by hydrolysis of a silicon compound in an oxygen-hydrogen flame, and wet-process silicas produced by hydrolyzing sodium silicate or the like in water, followed by neutralization. However, these silica powders have a number of silanol groups on their surface; therefore, when mixed into an organopolysiloxane compound as they are, followed by kneading, the silica powders may cause pseudo-crosslinking called structuring or crepe hardening during storage, resulting in serious lowering of fluidability and consistency of the compositions. In particular, in the case of rubber compositions, serious crepe hardening may take place.

As a silica powder which solved the above drawback of the prior art, there are known silicas treated with a chlorosilane of the formula: $R^4{}_3SiCl$, $R^4{}_3SiCl_2$ or $R^4SiCl_3$ where $R^4$ is a hydrocarbon group having from 1 to 8 carbon atoms, or a silazane compound of the formula: $(R^4{}_3Si)_2NH$ wherein $R^4$ is as defined above, thereby the silanol groups on the surface of the silica powders being silylated (See U.S. Pat. No. 3,532,664).

As a process of preparing an organopolysiloxane composition containing the treated silica, there is known a process in which a silica powder is mixed with a silicone rubber, and then the mixture is admixed with said silazane compound, a dialkylsilane diol, an alkoxysilane or the like, followed by reaction, and the silanol groups contained on the surface of the silica powder are thereby silylated in the course of the mixing step (See Japanese Patent Publication (KOKOKU) Nos. 58-8703(1983) and 56-34227(1981)).

In the organopolysiloxane compositions containing a treated silica whose surfaces have been silylated like the above, structuring during storage is reduced.

When a silica powder is treated as described above, however, there is a problem that the chlorosilane, the silazane or the like is reacted with the silica powder to by-produce HCl, $NH_3$, alcohol, etc. The removal of the by-product may require much time and energy. If the by-product remains in the resulting treated silica, the compositions prepared by adding the treated silica to a silicone oil or silicone gum are poor in heat resistance, durability of release property, durability of transparency, electric insulating properties, etc.

There is proposed a method of silylating silanol groups on the surfaces of a silica powder, using a silylketene acetal having the formula:

$$\begin{array}{c}H_3C\\ \phantom{xx}\diagdown\\ \phantom{xxxx}C=C\\ \phantom{xx}\diagup\phantom{xxxx}\diagdown\\ H_3C\phantom{xxxxxx}OR^5\end{array}\begin{array}{c}OSi(CH_3)_3\end{array}$$

wherein $R^5$ is a monovalent hydrocarbon group (Japanese Pre-examination Patent Publication (KOKAI) No. 2-59417 (1990) published on Feb. 28, 1990. This method has the disadvantage that an isobutyrate with disagreeable smell is by-produced.

SUMMARY OF THE INVENTION

Accordingly, an object of the present invention is to provide an organosilicone-treated silica of high quality, free of acids such as HCl, basic substance such as $NH_3$, or salts thereof, and free of substances with disagreeable smell.

Another object of the present invention is to provide an organopolysiloxane composition containing the above organosilicone-treated silica.

Still another object of the present invention is to provide a process of preparing the above composition.

According to the present invention, there is provide an organosilicone-treated silica obtained by treating (A) a silica powder having a specific surface area of at least 50 m²/g with (B) a triorgano(1-alkoxyvinyloxy)silane having the formula (I):

$$CH_2=\underset{\underset{OR^1}{|}}{C}-O-Si(R^2)_3 \qquad (I)$$

wherein $R^1$ is a monovalent hydrocarbon group of from 1 to 8 carbon atoms or an ether linkage-containing organic group of from 1 to 8 carbon atoms, and three $R^2$'s may be the same or different and are each a substituted or unsubstituted monovalent hydrocarbon group of from 1 to 18 carbon atoms or an ether linkage-containing organic group of from 1 to 18 carbon atoms.

Further, according to the present invention, there is provided an organopolysiloxane composition comprising:

(a) an organopolysiloxane having the general composition formula (II):

$$(R^3)_a(OH)_bSiO_{\frac{4-a-b}{2}} \qquad (II)$$

wherein $R^3$ is a substituted or unsubstituted monovalent hydrocarbon group of from 1 to 10 carbon atoms, a is a number of from 1.90 to 3.0, and b is a number of from 0 to 1.0, provided that a + b is in the range of from 1.90 to 3.0, (b) the organosilicone-treated silica powder as described above.

Still further, according to the present invention, there is also provided a process of preparing the above organopolysiloxane composition, comprising the step of kneading said (a) organopolysiloxane, said (A) silica powder and said (B) triorgano(1-alkoxyvinyloxy)silane.

The organosilicone-treated silica of the invention is of remarkably high quality, free of acids such as HCl, basic substances such as $NH_3$ or salts thereof by-produced in the process of production, and free of substances with pungent or disagreeable smell or corrosiveness such as isobutyrates. Thus, very few big particles form because the particles of the silica powder will hardly condense or agglomerate with each other, so that the treated silica powder is highly uniform in diameter. Since no substances with pungent or disagreeable smell or corrosiveness are by-produced in the production, the treated silica is advantageous with respect to health in working environment and selection of materials for equipment for production.

The organopolysiloxane composition of the present invention containing the above organosilicone-treated silica does not contain said by-products; hence pseudcrosslinking such as structuring or crepe hardening hardly takes place. Therefore, the composition does not change in viscosity, consistency, plasticity and the like, which is of practically high value. The composition is also excellent in heat resistance, durability of release properties, durability of transparency, and electrical properties such as electrical insulating properties.

DETAILED DESCRIPTION OF THE INVENTION

Organosilicone-treated silica

Figure 1:
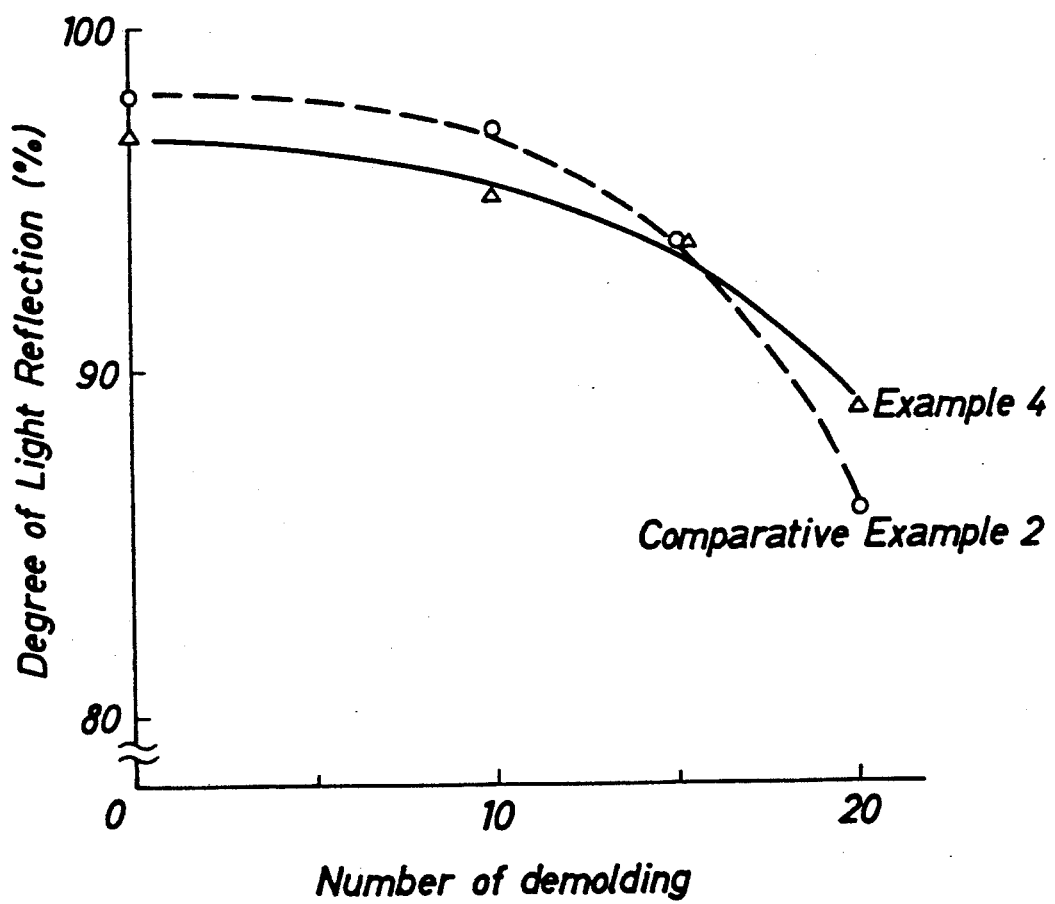
FIG. 1 is a graph showing the change of degree of light reflection on the surface of a molded product with respect to the number of demolding, measured in the release property test carried out for the cured product of the compositions prepared in Example 4 and Comparative Example 2.

The organosilicone-treated silica of the invention is prepared by treating said (A) silica powder with said (B) triorgano(1-alkoxyvinyloxy) silane, thereby the silanol groups on the surface being silylated.

(A) Silica powder

The silica powder of (A) includes, for example, dry process silicas such as fumed silica and wet process silicas. The silica powder has a specific surface area of at least 50 m²/g, preferably 100 m²/g or more, and more preferably from 200 to 400 m²/g in that the silicone rubbers containing the silica have a high tear resistance. If the specific surface area of the silica powder used is less than 50 m²/g, silicone rubbers containing the treated silica cannot acquire sufficiently improved mechanical strength. Examples of the silica powder include Aerosil-130, 200, 300 and 380 (tradenames, supplied by Degussa); MS-5, and MS-7 (tradenames, supplied by Cabot Corp.); Nipsil VN-3, LP, E220, A-330 (tradenames, supplied by Nippon Silica Co.).

(B) Triorgano(1-alkoxyvinyloxy)silane

The triorgano(1-alkoxyvinyloxy)silane of (B) used in the invention is the compound of said formula (I). In the formula (I), $R^1$ is a monovalent hydrocarbon group having from 1 to 8, preferably from 1 to 3, carbon atoms or an ether linkage-containing organic group having from 1 to 8, preferably from 1 to 3, carbon atoms. The monovalent hydrocarbon group includes, for example, alkyl groups such as methyl, ethyl and propyl; aliphatic or alicyclic unsaturated hydrocarbon groups such as vinyl, allyl, cyclopentenyl and cyclohexenyl; aromatic hydrocarbon groups such as phenyl, tolyl and benzyl. The ether linkage-containing organic group includes, for example, methoxyethyl, ethoxyethyl, and allyloxyethyl.

The three $R^2$ in the formula (I) may be the same or different and are each a substituted or unsubstituted monovalent hydrocarbon group of from 1 to 18, preferably from 1 to 3, carbon atoms, or an ether linkage-containing organic group having 1 to 18, preferably from 1 to 3, carbon atoms. The unsubstituted monovalent hydrocarbon group includes, for example, alkyl groups such as methyl ethyl and propyl; aliphatic or alicyclic unsaturated hydrocarbon groups such as vinyl, allyl, cyclopentenyl and cyclohexenyl; aromatic hydrocarbon groups such as phenyl, tolyl, and benzyl. The substituted monovalent hydrocarbon group includes, for example, those in which part or all of the hydrogen atoms bonded to a carbon atom of the above unsubstituted hydrocarbon groups have been substituted with a halogen atom such as chlorine or fluorine, the cyano group, the nitrile group, or an alkoxyl group. The fluorine-substituted hydrocarbon group and the ether linkage-containing organic group among these include, for example, the groups having the formulas:

wherein p is an integer of from 1 to 12,

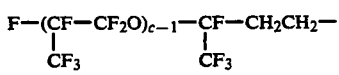

wherein c in an integer of from 1 to 5,

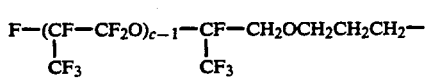

wherein c is as defined above, and

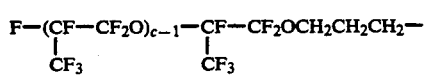

wherein c is as defined above, and methoxyethyl, ethoxyethyl and allyloxyethyl groups.

Examples of the triorgano(1-alkoxyvinyloxy)silane having the formula (I) include the compounds having the following formulas:

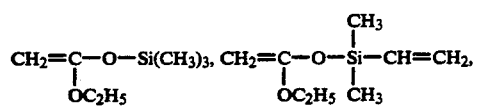

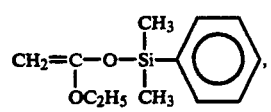

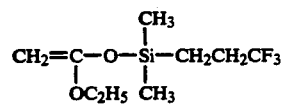

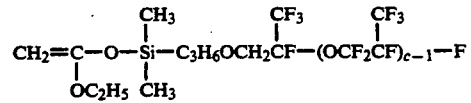

where c is an integer of from 2 to 5,

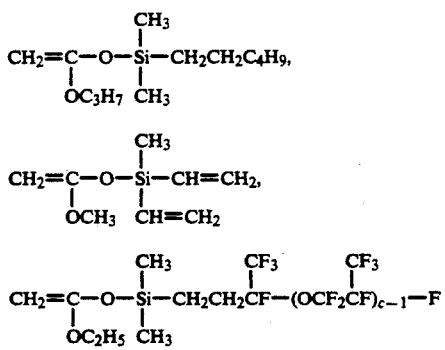

wherein c is as defined above. The triorgano(1-alkoxyvinyloxy)silane described above may be used singly or in combination of two or more.

Preferably, the triorgano(1-alkoxyvinyloxy)silane has a low molecular weight, because an acetate by-produced or unreacted triorgano(1-alkoxyvinyloxy)silane can be removed with ease after the silica powder of (A) is treated therewith. For this reason, in the formula (I), $R^1$ is preferably the methyl group, the ethyl group or the propyl group, and $R^2$ is preferably the methyl group or the vinyl group.

For preparing the triorgano(1alkoxyvinyloxy)silane of the formula (I), for instance, first diisopropylamine is reacted with butyl lithium to produce a LDA reagent [(isopropyl)$_2$N.Li]. The acetate compound of the formula:

$$H_3C-\overset{O}{\overset{\|}{C}}-O-R^1$$

wherein $R^1$ is as defined in respect of the formula (I), is then added to the reaction mixture dropwise at a low temperature of from $-70°$ to $-80°$ C. to allow reaction to proceed to produce a lithium enolate compound having the formula:

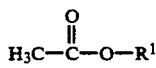

Subsequently, a triorganohalosilane having the formula:

$$XSi(R^2)_3$$

wherein X is a halogen atom, and $R^2$ is as defined in respect of the formula (I), is added dropwise at a low temperature of from $-70°$ to $-80°$ C. to the reaction mixture to allow reaction to proceed, thereby the aimed compound being produced. The triorgano(1-alkoxyvinyloxy)silane can be isolated by subjecting it filtration, followed by distillation (Ainsworth et al., J. Organomet Chem. 46 (1972), pp. 59–71).

In preparing the treated silica of the invention, the triorgano(1-alkoxyvinyloxy)silane of (B) is normally used in an amount of preferably from 0.5 to 100 parts by weight, more preferably from 10 to 50 parts by weight, per 100 parts by weight of the silica powder of (A). If the triorgano(1-alkoxyvinyloxy)silane is used in too small an amount, silylation of the silanol groups on the surfaces of silica powder does not sufficiently proceed, resulting in the disadvantages that when the resulting treated silica powder is added to a rubber composition, crepe hardening of the composition may increase, or that when added to one-pack moisture curing type RTV silicone rubber composition, much crosslinking agent may be required to be added to prevent increase in viscosity with time of the composition. Use of the triorgano(1-alkoxyvinyloxy)silane in too large an amount, results in the disadvantage that unreacted compound to be removed after the completion of the reaction will increase.

Preparation of the organosilicone-treated silica

Reaction required for preparation of the organosilicone-treated silica of the invention can be performed only by adding the triorgano(1-alkoxyvinyloxy)silane of (B) dropwise or by spraying to the silica powder of (A) charged in a given amount in a reaction vessel, under stirring at room temperature. The reaction normally proceed, releasing heat and by-producing an acetate compound. This reaction is expressed, for example, by the following equation:

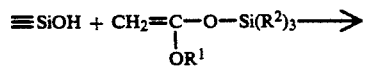

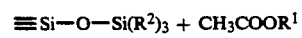

wherein $R^1$ and $R^2$ are the same as defined in respect of said formula (I). The reaction is allowed to proceed under the conditions above for tens of minutes to several days. Thereafter, by-products such as the acetate compound and unreacted organo(1-alkoxyvinyloxy)silane are removed, and the organosilicone-treated silica can be thereby obtained. The above reaction can proceed even at room temperature. It can be accelerated by heating at a temperature of above room temperature and about 200° C. or less; for instance, reaction time can be reduced to within one hour. Preferably, prior to the reaction, unstable siloxane linkages on the silica powder of (A) is previously converted into silanol groups, and the silica powder is left to stand in an atmosphere with an RH of about 80% to regulate the moisture content, so that silylation proceeds sufficiently.

By using a triorgano(1-alkoxyvinyloxy)silane containing a functional group such as the vinyl group as an organic group as at least a part of (B), it is possible to introduce the functional group onto the surface of the resulting treated silica powder in a given amount.

In the preparation of the treated silica powder, a suitable inactive organic solvent can be used as required. The organic solvent which may be used includes, for example, hydrocarbon solvents such as hexane, benzene, toluene, and xylene; halogenated hydrocarbon solvents such as trichloroethane, and trichlorotrifluoroethane. These may be used singly or in combination of two or more.

Organopolysiloxane composition

The organosilicone-treated silica powder as prepared above may be added to an organopolysiloxane to prepare, for example, an organopolysiloxane composition comprising:

(a) an organopolysiloxane having the general composition formula (II):

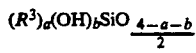 (II)

wherein $R^3$ is a substituted or unsubstituted monovalent hydrocarbon group of from 1 to 10 carbon atoms, a is a number of from 1.90 to 3.0, and b is a number of from 0 to 1.0, provided that a+b is in the range of from 1.90 to 3.0, and (b) the organosilicone-treated silica powder as described above.

In the general composition formula (II) representing said (a) organopolysiloxane, $R^3$ is a substituted or unsubstituted monovalent hydrocarbon group having from 1 to 10, preferably from 1 to 6, carbon atoms, and includes, for example, alkyl groups such as methyl, ethyl and propyl; aliphatic or alicyclic unsaturated hydrocarbon groups such as vinyl, allyl, cyclopentenyl and hexenyl; aromatic hydrocarbon groups such as phenyl, tolyl, xylyl and benzyl; and corresponding substituted hydrocarbon groups in which part or all of the hydrogen atoms bonded to said hydrocarbon groups have been substituted by a halogen atom such as chlorine and fluorine, the cyano group, an alkoxyl group or an amino group, e.g. a chloropropyl group, a cyanoethyl group, a methoxyethyl group and the 3,3,3-trifluoropropyl group. The symbol a is a number of from 1.90 to 3.0, preferably from 1.96 to 2.40; b is a number of from 0. to 1.0, preferably from 0 to 0.40; a+b ranges from 1.90 to 3.0, preferably from 1.96 to 2.40. The organopolysiloxanes of (a) may be used singly or in combination of two or more.

The organopolysiloxane of (a) has normally a polymerization degree of not higher than 10,000, including from a liquid one with a low viscosity to a gum-like one. Particularly, where a liquid silicone rubber composition is prepared, an organopolysiloxane having a viscosity at 25° C. of from 500 to 100,000 cSt is preferred.

Example of the (a) organopolysiloxane include the compounds having the formulas below.

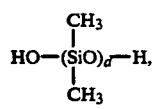

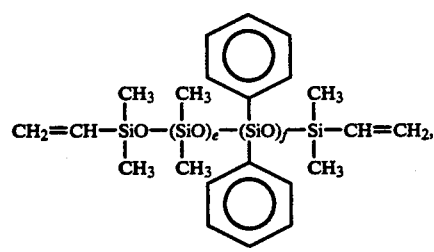

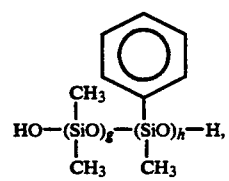

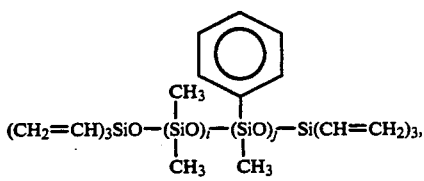

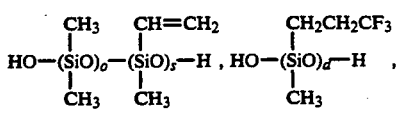

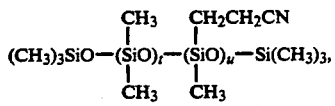

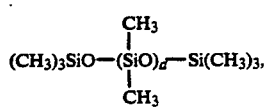

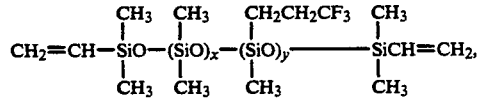

and

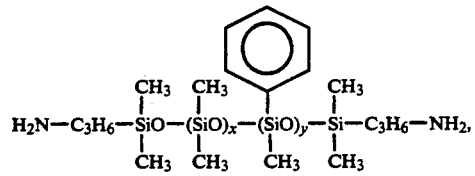

provided that in the above formulas d, e, f, g, h, i, j, o, s, t, u, x and y are each 0 or an positive integer, for example an integer of from 50 to 1,000.

The organopolysiloxane of (a) can be prepared commercially by known methods. For example, it can be prepared by subjecting a cyclic siloxane having the formula (VIII):

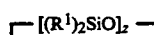 (VII)

wherein $R^1$ is as defined in respect of said general composition formula (I), and z is, for instance, an integer of from 3 to 8, such as cyclotriorganosiloxanes and cyclotetraorganosiloxanes, and a triorganodisiloxane or a small amount of water to equilibration reaction, ring-opening polymerization or the like in the presence of an acid or alkaline catalyst.

The organopolysiloxane composition of the invention normally contains form 1 to 100 parts by weight, preferably from 10 to 50 parts by weight, of said (b) organosilicone-treated silica powder per 100 parts by weight of said (a) organopolysiloxane.

Preparation of the organopolysiloxane composition

Preparation of the organopolysiloxane composition can be carried out, for example, as described above, by a process which comprises treating the silica powder of (A) with the triorgano(1-alkoxyvinyloxy)silane to produce the organosilicone-treated silica powder of (b), and mixing the organosilicone-treated silica with said (a) organopolysiloxane in a given amount. The mixing may be carried out by conventional methods, for instance, by using a mixer such as a planetary mixer, a kneader or a Banbury mixer, or a three roll mill or a two roll mill.

Alternatively, the preparation of the organopolysiloxane composition can be performed by methods in which, to the (a) organopolysiloxane, the (A) silica powder and (B) triorgano(1-alkoxyvinyloxy)silane are added directly, followed by kneading. Specifically, for instance, the preparation can be performed by a process comprising the step of kneading a mixture comprising:

100 parts by weight of the (a) organopolysiloxane having said general formula (II), from 10 to 100 parts by weight of the (A) silica powder with a specific surface area of at least 50 $m^2/g$, and from 0.1 to 200 parts by weight of the (B) triorgano(1-alkoxyvinyloxy)silane having said formula (I).

This process is described below. However, since it may be carried out in the same manner as in the process described above, except for the preferable amount of the silica powder used, the amount of the triorgano(1-alkoxyvinyloxy)silane used, and mixing and kneading the ingredients directly, the process is described below with respect to points to be noted particularly.

In the preparation process, for example, the amount of the (A) silica powder is from 10 to 100 parts by weight, preferably from 20 to 50 parts by weight, per 100 parts by weight of the (a) organopolysiloxane. The amount of the (B) triorgano(1-alkoxyvinyloxy)silane is, for example, from 0.1 to 200 parts by weight, preferably from 2 to 50 parts by weight, per 100 parts by weight of the (a) organopolysiloxane. If the amount of the (B) triorgano(1-alkoxyvinyloxy)silane is too small, silylation of the silanols on the surfaces of the silica powder therewith is not sufficiently performed; if the amount too large, post-treatment after the reaction, such as recovery of unreacted silane of (B), is time-consuming and requires much energy, which is disadvantageous economically.

According to the preparation process for the organopolysiloxane composition, mixing the ingredients (a), (A) and (B) at room temperature in a closed atmosphere will allow the silanol groups on the surfaces of the (A) silica powder and the (B) triorgano(1-alkoxyvinyloxy)silane to react, so that silylation of the silanol groups proceeds. If the mixture is heated, for example, at about 100° C., the reaction is accelerated. Subsequently, the reaction mixture may be heated, for example, to about 160° C.; thus an acetate compound formed by the reaction, silanols and siloxanes with low molecular weights and the unreacted triorgano(1-alkoxyvinyloxy)silane may be removed under heating or under reduced pressure and heating.

In order to cure the organopolysiloxane composition obtained as described above, a suitable crosslinking agent, a catalyst, etc. may be added thereto as conventionally performed, depending on the purpose, the curing method, and the kind, etc. of the (a) organopolysiloxane, the (A) silica powder and (B) triorgano(1-alkoxyvinyloxy)silane. For example, in the case of heat-cure rubber, an organic peroxide may be added, and curing or crosslinking can be performed by heating under pressure. In the case of addition cure-type liquid rubber, an organopolysiloxane containing a vinyl group is used as the (A) organopolysiloxane, a polyfunctional hydrogenpolysiloxane is used as a crosslinking agent, and a platinum catalyst is used in a catalytic amount; the composition obtained can be cured at room temperature or under heating. In the case of condensation-type liquid rubber, a silanol group-terminated siloxane is used as the (A) organopolysiloxane, and a polyfunctional silicon compound crosslinkable with a silanol group such as acetoxysilanes, alkoxysilanes or a partial hydrolyzate thereof is used; thus a curable composition can be obtained. These methods of making organopolysiloxane compositions curable are well-known in the art.

The organopolysiloxane composition of the present invention may contain any additives which are conventionally added as desired according to purposes, required performance and properties of organopolysiloxane compositions. The additives include, for example, pigments, heat resistance improvers, adhesion aids, release agents and oil resistance improvers.

EXAMPLES

The present invention will now be described in detail with reference to working examples and comparative examples. In the following, viscosity given indicates the value measured at 25° C.

EXAMPLE 1

A flask was charged with 20 g of silica powder with a specific surface area of 310 $m^2/g$ (Aerosil 300, tradename, supplied by Nippon Aerosil Co.), to which 5.0 g of trimethyl(1-ethoxyvinyloxy)silane was added dropwise gradually under stirring at room temperature to allow reaction to proceed. Immediately, generation of heat and ethyl acetate smell was recognized. The reaction mixture was stirred for one hour in a closed atmosphere. After the reaction mixture was allowed to stand at room temperature for 16 hours for maturation, it was transferred to an enameled dish, and then air-dried in a draft chamber for about 2 hours, followed by heat-treatment at 150° C. for about 16 hours in a hot-air circulating oven to remove by-produced ethyl acetate and unreacted silane. Thus, 22.3 g of a treated silica in the form of fine white powder was obtained.

The treated silica obtained was measured for specific surface area, carbon content, chlorine content and ammonia content, which were found to be 167 $m^2/g$, 4.8% by weight, 25 ppm and not more than 1 ppm, respectively.

Further, 1.0 g of the treated silica, 40 g of toluene and 100 g of deionized water were placed in a vessel, and shaken for one hour. Subsequently, the water separated as the lower layer was tested for electrical conductivity (hereinafter, referred to as "extracted water conductivity") to be 1.1 $\mu S/cm$.

The treated silica was tested for wettability with water by placing some treated silica and water in a bottle, and shaking the bottle. All the silica powder floated on the surface of the water, indicating that the treated silica powder has good water repellency.

The treated silica powder was subjected to a sieve of 50 mesh. The oversize fraction was 0.6%.

COMPARATIVE EXAMPLE 1

A flask was charged with 20 g of silica powder which is the same as used in Example 1, to which 2 g of deionized water was added dropwise at room temperature under stirring, and then 4.0 g of hexamethyldisilazane was further added dropwise gradually. Mild heat generation and generation of ammonia smell were recognized. Subsequently, the reaction mixture was stirred for one hour in a closed atmosphere, and then was left to stand at room temperature for about 16 hours for maturation. The reaction mixture obtained was treated in the same manner as in Example 1 to give 22.0 g of a treated silica.

The treated silica obtained was measured for specific surface area, carbon content, chlorine content, ammonia content and extracted water conductivity, which were found to be 186 m$^2$/g, 4.3% by weight, 30 ppm, 35 ppm and 2.3 μS/cm, respectively. The treated silica was tested for wettability with water in the same manner as in Example 1. All the silica powder floated on the surface of the water, indicating that the treated silica powder has good water repellency. The oversize fraction with respect to the sieve of 50 mesh was 5%.

EXAMPLE 2

A flask was charged with 10 g of a silica powder with a specific surface area of 200 m$^2$/g (Aerosil 200, tradename, supplied by Nippon Aerosil Co.), to which 2.0 g of a mixture of 50% by weight of the compound having the formula:

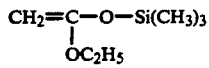

and 50% by weight of the compound having the formula:

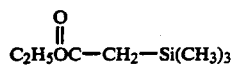

was added dropwise gradually under stirring at room temperature. Immediately, generation of heat and ethyl acetate smell was recognized. Subsequently, the reaction mixture was stirred in a closed atmosphere for 30 minutes, and then heated up to 100° C. and stirred for about 2 hours, so that a reaction mixture in the form of powder was obtained. This powder was transferred to an aluminum tray, which was then placed in a vacuum drying chamber at 120° C. for about 12 hours. Thus, the by-produced ethyl acetate and unreacted silane were removed, and 10.7 g of a treated silica in the form of fine white powder was thereby obtained.

The treated silica obtained was measured for specific surface area, carbon content, chlorine content, and ammonia content, which were found to be 120 m$^2$/g, 3.3% by weight, 25 ppm and not more than 1 ppm, respectively. The treated silica was tested for wettability with water in the same manner as in Example 1. All the silica powder floated on the surface of the water, indicating that the treated silica powder has good water repellency.

EXAMPLE 3

A flask was charged with 10 g of a silica powder with a specific surface area of 200 m$^2$/g (Aerosil 200, tradename, supplied by Nippon Aerosil Co.), to which 10.4 g of fluorine-containing ethoxyvinyloxysilane having the formula:

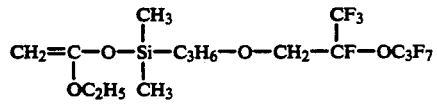

was added dropwise gradually under stirring at room temperature. Immediately, generation of heat and ethyl acetate smell was recognized. Subsequently, the reaction mixture was stirred in a closed atmosphere for one hour, and then allowed to stand at room temperature for maturation for about 16 hours, so that a reaction mixture in the form of powder was obtained. This powder was transferred to an aluminum tray, which was placed in a vacuum drying chamber at 150° C. for about 16 hours. Thus, the by-produced ethyl acetate and unreacted silane were removed, and 14.9 g of a treated silica in the form of fine white powder was obtained.

The treated silica obtained was measured for specific surface area, carbon content, fluorine content, chlorine content and ammonia content, which were found to be 110 m$^2$/g, 9.7% by weight, 15.0% by weight, 20 ppm and not more than 1 ppm, respectively. The treated silica was tested for wettability with water in the same manner as in Example 1. All the silica powder floated on the surface of the water, indicating that the treated silica powder has good water repellency.

EXAMPLE 4

100 parts by weight of a dimethylpolysiloxane end-blocked with the vinyl group at both ends having a viscosity of 5,000 cSt, 10 parts by weight of the treated silica powder obtained in Example 1, 0.1 part by weight of a platinum catalyst substantially free from chlorine (Pt content: 1.0% by weight, toluene solution), prepared from the vinylsiloxane having the formula:

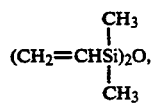

and a chloroplatinic acid, and 0.2 part by weight of cyclotetrasiloxane of the formula:

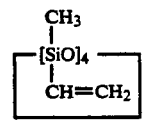

were mixed uniformly, and kneaded with a three roll mill to give a kneaded product in which the ingredients are uniformly dispersed. To 110.3 parts by weight of the kneaded product was added 2.3 parts by weight of the methylhydrogenpolysiloxane having the formula on average:

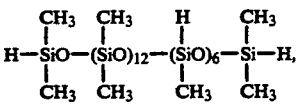

followed by mixing and defoaming under vacuum to give a composition.

The cured product of the composition obtained was tested for release properties, hardness, elongation, tensile strength and specific gravity in accordance with the methods below.

Test of release properties

The composition defoamed under vacuum was applied to the surfaces of a metal block covered with mirror surfaces, measuring 5×5×0.5 (cm) placed in an acrylic resin-made, box-shaped mold measuring 7×7×1.5 (cm). The applied composition was allowed to stand at room temperature for 24 hours and thereby cured. The cured product was then taken out of the mold, and then matured for curing for two days, so that a negative mold was obtained. Into the negative mold was poured a resin composition prepared by mixing a curing agent containing triethylenetetramine as its main ingredient into a liquid bisphenol-type epoxy resin. The resin composition was cured at 80° C. for 30 minutes. The molded product thus formed was then demolded. The procedures from pouring the resin composition to demolding a molded product were repeated, and release properties and durability of release properties of the negative mold were evaluated in accordance with the criteria below.

(1) Release properties

Release properties were evaluated according to the following criteria:
A: There is extremely slight resistance when the cured molded product is demolded.
B: There is medium resistance when the cured molded product is demolded.
C: There is considerable resistance when the cured molded product is demolded.

(2) Durability of the release properties

The change of degree of light reflection on the surface of the molded product with respect to the number of demolding was measured. The results over the demolding number of up to 20 are shown in FIG. 1.

Hardness, elongation, tensile strength and specific gravity

The composition was put in a metal mold measuring 12×15×0.2 (cm), and then the upper surface was smoothed with a stainless steel-made plate. The composition was allowed to stand at room temperature for 24 hours for curing. Thereafter, the cured composition was taken off from the metal mold, and further matured or cured for two days to give a cured sheet. From the cured sheet, dumbbell-shaped specimens were stamped out, and tested for hardness, elongation and tensile strength in accordance with JIS K 6301. Hardness was measured using A-type spring hardness tester defined in JIS K 6301. The specific gravity of the cured sheet was also measured.

The results are given in Table 1.

Comparative Example 2

A composition was prepared in the same manner as in Example 4, except that the treated silica used in Example 4 was replaced by the treated silica obtained in Comparative Example 1. The cured product of the composition was tested for release properties, durability of the release properties, hardness, elongation, tensile strength and specific gravity. The results are given in Table 1 and FIG. 1.

TABLE 1

|  | Example 4 | Comparative Example 2 |
| --- | --- | --- |
| Release properties | A | B |
| Mechanical properties |  |  |
| Hardness | 25 | 26 |
| Elongation (%) | 315 | 300 |

TABLE 1-continued

|  | Example 4 | Comparative Example 2 |
| --- | --- | --- |
| Tensile strength (kg/cm$^2$) | 15 | 14 |
| Specific gravity | 1.02 | 1.02 |

EXAMPLE 5

100 parts by weight of dimethylpolysiloxane end-blocked with the hydroxyl group at both ends having 20,200 cSt, 15 parts by weight of the treated silica obtained in Example 1, 7.0 parts by weight of vinyltriisopropenyloxysilane and 0.5 part by weight of the guanidyl group-containing organic silicon compound having the formula:

$$[(CH_3)_2N-]_2C=N-C_3H_6-Si(-OCH_3)_3$$

were mixed in the condition in which moisture is shielded, to prepare a composition.

The composition obtained was formed into a sheet 2 mm thick, which was cured by allowing it to stand in an atmosphere of 20° C. and RH 55% to produce a cured sheet. From the cured sheet, dumbbell-shaped specimens were stamped out, and tested for hardness, tensile strength and elongation in accordance with JIS K 6301. Moreover, a cured sheet prepared in the same manner as above was aged under heating at 230° C. for 7 days, and thereafter dumbbell-shaped specimens were stamped out from the aged cured sheet, and tested for hardness, tensile strength and elongation in accordance with JIS K 6301. The results were used for evaluating heat resistance.

Further, the composition obtained was formed into a sheet with a thickness of 1 mm, which was cured by allowing it to stand in an atmosphere of 20° C. and RH 55% for 7 days, to produce a cured sheet. This cured sheet was tested for volume resistivity, dielectric breakdown strength, dielectric constant and dielectric loss tangent in accordance with JIS C 2123. The results are given in Table 2.

COMPARATIVE EXAMPLE 3

A composition was prepared in the same manner as in Example 5, except that the treated silica used in Example 5 was replaced with that obtained in Comparative Example 1. Hardness, elongation and tensile strength of the cured product, and these mechanical properties of the cured product aged under heating were measured in the same manner as in Example 4. Moreover, volume resistivity, dielectric breakdown strength, dielectric constant and dielectric loss tangent of the cured product were measured in the same manner as in Example 5. The results are given in Table 2.

COMPARATIVE EXAMPLE 4

A composition was prepared in the same manner as in Example 4, except that the treated silica prepared in Example 1 was replaced with a silica treated with dimethyldichlorosilane R-972 (tradename, supplied by Nippon Aerosil Co.). Hardness, elongation and tensile strength of the cured product, and these mechanical properties of the cured product aged under heating were measured in the same manner as in Example 4. Moreover, volume resistivity, dielectric breakdown strength, dielectric constant and dielectric loss tangent of the cured product were measured in the same manner as in Example 5. The results are given in Table 2.

TABLE 2

| | | Comparative | |
|---|---|---|---|
| | Exam. 5 | Exam. 3 | Exam. 4 |
| Mechanical properties | | | |
| Hardness | 27 | 28 | 31 |
| Tensile strength (kgf/cm$^2$) | 23 | 20 | 21 |
| Elongation (%) | 420 | 380 | 370 |
| Mechanical properties after aging under heating | | | |
| Hardness | 30 | 35 | 38 |
| Tensile strength (kgf/cm$^2$) | 22 | 21 | 19 |
| Elongation (%) | 320 | 180 | 200 |
| Electrical properties | | | |
| Volume resistivity ($\times 10^{14} \cdot \Omega$cm) | 5.8 | 1.4 | 1.1 |
| Dielectric breakdown strength (kV/mm) | 29 | 24 | 25 |
| Dielectric constant* | 2.63 | 2.98 | 2.95 |
| Dielectric loss tangent* | 0.0008 | 0.003 | 0.002 |

Remarks:
*measured at 50 Hz

EXAMPLE 6

A kneader was charged with 90 parts by weight of dimethylpolysiloxane endblocked with the vinyl group at both ends having a viscosity of 10,000 cSt and 7.5 parts by weight of trimethyl(1-ethoxyvinyloxy)silane having the formula:

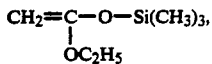

which were then mixed uniformly. To the mixture, 30 parts by weight of silica powder (Aerosil 200, tradename, supplied by Nippon Aerosil Co.) was added gradually. Generation of heat and generation of ethyl acetate smell were recognized as the addition of the silica powder was proceeded. After the addition of all of the silica powder, the mixture was further mixed for another one hour by stirring at room temperature in a closed atmosphere, followed by mixing at 80° C. for one hour for maturation. Subsequently, the cover of the kneader was opened, and the mixture was heated at 160° C. for 3 hours with stirring in order to evaporate by-produced ethyl acetate and unreacted silane, thereby a composition being obtained.

To 120 parts by weight of the composition thus obtained, were added 10 parts by weight of the same dimethylpolysiloxane of having a viscosity of 10,000 cSt as mentioned above, 0.2 part by weight of the same platinum catalyst as used in Example 4, and 0.15 part by weight of 50% ethynyl cyclohexanol solution in toluene. The mixture was kneaded uniformly with a three roll mill to prepare a rubber composition.

The viscosity of the composition obtained was measured to be 7,400 P. After accelerated aging at 105° C. for 6 hours, the composition was measured to be 8,900 P. While the tested composition has originally a high viscosity, it exhibited good viscosity stability.

To 130 parts by weight of the rubber composition, 1.7 parts by weight of the same methylhydrogenpolysiloxane as used in Example 4 was added, and they were mixed uniformly, defoamed, poured into a metal mold, and presscured at 150° C. for 10 minutes to form two molded sheets measuring 12×15×0.2 (cm). One of the sheets was postcured at 200° C. for 4 hours, but the other sheet was not postcured. Then, mechanical properties of the two sheets were measured in accordance with JIS K 6301. The results are given in Table 3.

TABLE 3

| | After press cure | After postcure |
|---|---|---|
| Hardness | 37 | 39 |
| Elongation (%) | 710 | 665 |
| Tensile strength (kg/cm$^2$) | 93 | 101 |
| Tear resistance (kg/cm) | 15 | 14 |

We claim:
1. An organosilicone-treated silica obtained by treating
   (A) a silica powder having a specific surface area S of at least 50 m$^2$/g with
   (B) a triorgano(1-alkoxyvinyloxy)silane having the formula (I):

wherein R$^1$ is a monovalent hydrocarbon group of from 1 to 8 carbon atoms or an ether linkage-containing organic group having from 1 to 8 carbon atoms, and three R$^2$'s may be the same or different and are each a substituted or unsubstituted monovalent hydrocarbon group of from 1 to 18 carbon atoms or an ether linkage-containing organic group having from 1 to 18 carbon atoms.

2. The organosilicone-treated silica of claim 1, wherein said (B) triorgano(1-alkoxyvinyloxy)silane is used in an amount of from 0.5 to 100 parts by weight per 100 parts by weight of said (A) silica.

3. The organosilicone-treated silica of claim 1, wherein said (B) triorgano(1-alkoxyvinyloxy)silane is used in an amount of from 10 to 50 parts by weight per 100 parts by weight of said (A) silica.

4. The organosilicone-treated silica of claim 1, wherein said (B) triorgano(1-alkoxyvinyloxy)silane is represented by said formula (I) wherein said R$^1$ is a group selected from the group consisting of alkyl groups, aliphatic or alicyclic unsaturated hydrocarbon groups and aromatic hydrocarbon groups.

5. The organosilicone-treated silica of claim 1, wherein said (B) triorgano(1-alkoxyvinyloxy)silane is represented by said formula (I) wherein said R$^1$ is a group selected from the group consisting of the methoxyethyl, ethoxyethyl, and allyloxyethyl groups.

6. The organosilicone-treated silica of claim 1, wherein said (B) triorgano(1-alkoxyvinyloxy)silane is represented by said formula (I) wherein said R$^2$ is a monovalent hydrocarbon group having from 1 to 18 carbon atoms.

7. The organosilicone-treated silica of claim 1, wherein said (B) triorgano(1-alkoxyvinyloxy)silane is represented by said formula (I) wherein said R$^2$ is a group selected from the groups represented by the following formulas:

wherein p is an integer of from 1 to 12,

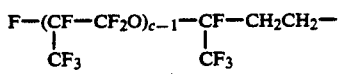

wherein c in an integer of from 1 to 5,

wherein c is as defined above, and

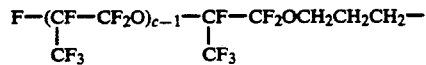

wherein c is as defined above.

8. The organosilicone-treated silica of claim 1, wherein said (B) triorgano(1-alkoxyvinyloxy)silane is represented by said formula (I) wherein $R^1$ is the methyl group, the ethyl group or a propyl group, and said $R^2$ is the methyl group or the vinyl group.

9. An organopolysiloxane composition comprising:
   (a) an organopolysiloxane having the general compositon formula (II):

wherein $R^3$ is a substituted or unsubstituted monovalent hydrocarbon group of from 1 to 10 carbon atoms, a is a number of from 1.90 to 3.0, and b is a number of from 0 to 1.0, provided that a+b is in the range of from 1.90 to 3.0, and (b) an organosilicone-treated silica obtained by treating
   (A) a silica powder having a specific surface area of at least 50 m²/g with
   (B) a triorgano(1-alkoxyvinyloxy)silane having the formula (I):

wherein $R^1$ is a monovalent hydrocarbon group of from 1 to 8 carbon atoms or an ether linkage-containing organic group having from 1 to 8 carbon atoms, and three $R^2$'s may be the same or different and are each a substituted or unsubstituted monovalent hydrocarbon group of from 1 to 18 carbon atoms or an ether linkage-containing organic group having from 1 to 18 carbon atoms.

10. The organopolysiloxane composition of claim 9, wherein said (b) organosilicone-treated silica is present in an amount of from 1 to 100 parts by weight per 100 parts by weight of said (a) organopolysiloxane.

11. A process of preparing an organopolysiloxane composition claimed in claim 9, comprising the step of kneading a mixture comprising:
   100 parts by weight of the (a) organopolysiloxane having said general formula (II),
   from 10 to 100 parts by weight of said (A) silica powder with a specific surface area of at least 50 m²/g, and
   from 0.1 to 200 parts by weight of said (B) triorgano(1-alkoxyvinyloxy)silane having said formula (I).

* * * * *